Figure 1:
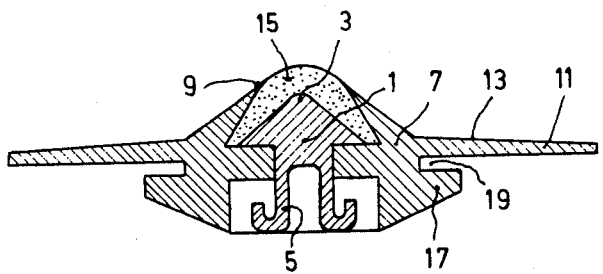

United States Patent
Vredenbregt

[11] 3,967,628
[45] July 6, 1976

[54] SKIN ELECTRODE

[75] Inventor: Jakob Vredenbregt, Eindhoven, Netherlands

[73] Assignee: U.S. Philips Corporation, New York, N.Y.

[22] Filed: Feb. 3, 1975

[21] Appl. No.: 546,795

[30] Foreign Application Priority Data
Feb. 21, 1974 Netherlands.................. 7402355

[52] U.S. Cl................................. 128/417; 128/418
[51] Int. Cl.².................................................. A61N 1/04
[58] Field of Search........... 128/417, 418, 416, 404, 128/410, 411, 2.06 E, 2.1 E, DIG. 4, 172.1

[56] References Cited
UNITED STATES PATENTS

| 990,158 | 4/1911 | Moses | 128/417 |
|---|---|---|---|
| 2,318,207 | 5/1943 | Ellis | 128/418 |
| 3,029,820 | 4/1962 | Franklin | 128/404 |
| 3,187,745 | 6/1965 | Baum et al. | 128/417 |
| 3,543,761 | 12/1970 | Bradley | 128/418 |
| 3,612,061 | 10/1971 | Collin et al. | 128/418 |
| 3,795,241 | 3/1974 | Golovko | 128/2.06 E |
| 3,862,627 | 1/1975 | Hans, Sr. | 128/2.06 E |
| 3,882,853 | 5/1975 | Gofman et al. | 128/2.06 E |

Primary Examiner—Robert W. Michell
Assistant Examiner—Lee S. Cohen
Attorney, Agent, or Firm—Frank R. Trifari; Ronald L. Drumheller

[57] ABSTRACT

A skin electrode, comprising a core provided with a pointed portion which projects through an opening in a jacket which is made of a flexible, non-slipping material and which has an integral flat edge. Because of its shape and the material properties, the electrode can be applied on the skin under a comparatively low pressure without sliding.

4 Claims, 2 Drawing Figures

U.S. Patent   July 6, 1976   3,967,628

SKIN ELECTRODE

The invention relates to an electrode to be applied to the skin of a patient.

Electrodes of this kind are used, for example, in conjunction with an apparatus for stimulating nerves situated directly below the skin such as described in the published Netherlands Patent Application 7,102,659. It was found in practice that the electrodes known to be used for this purpose tend to slide during use. As a result, the distance with respect to the nerve to be stimulated is increased, so that the pursued effect is not realized. The sliding can be counteracted to some extent by pressing the electrode against the skin under great pressure or by gluing it to the skin, but this is annoying to the patient and may even be painful. The invention has for its object to provide an electrode which does not slide after it has been quickly and simply applied on the skin under an only comparatively small pressure. To this end, the electrode according to the invention is characterized in that the electrode comprises an electrically conductive core which is provided with a pointed portion which projects through an opening in a jacket of a flexible, non-slipping material, the said jacket being provided with a substantially flat edge of the same material which extends in a plane approximately perpendicular to the direction in which the pointed portion projects. The use of the term "pointed" in this context does not imply that the relevant portion of the core should be needlesharp. A "tip" having a rounding radius of about 1 mm was found to be suitable for this purpose.

When the electrode is applied, the pointed portion is slightly pressed into the tissue, without the patient being annoyed thereby. In combination with the friction between the skin and the non-slipping surface of the edge and the jacket, lateral displacement of the electrode is thus completely precluded. The material of the jacket is preferably silicon rubber, and the edge may be roughened to increase the friction even further.

In order to ensure proper and uniform electrical contact between the electrode and the skin, between the jacket and the pointed portion of the core there is preferably present a space in which a piece of spongy material is clamped to cover the pointed portion. This material can be saturated in known manner with water or an electrode paste.

The invention will be described in detail hereinafter with reference to the drawing.

FIG. 1 is a sectional view of an embodiment.

Figure 2:
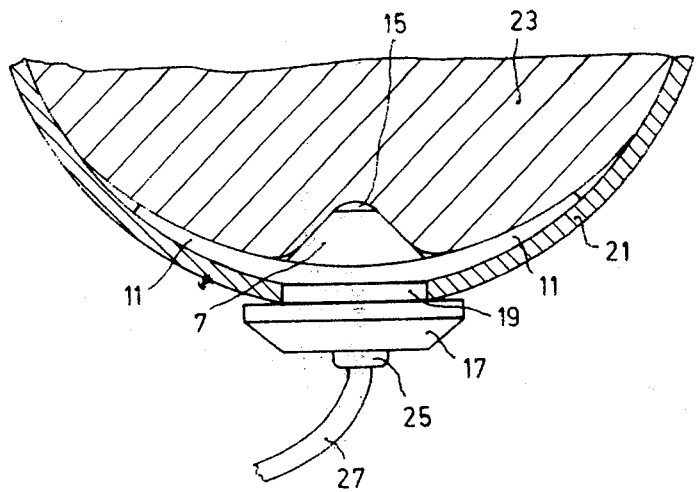

FIG. 2 diagrammatically illustrates how the electrode of FIG. 1 can be attached to a patient's leg.

The disc-shaped electrode shown in FIG. 1 comprises a core 1, preferably made of stainless steel, having a pointed portion 3 which is shaped as a cone in this embodiment. On the opposite side of the core 1 there is provided a connection 5 for connection to a generator for stimulation pulses. The core 1 is enveloped by a jacket 7 of silicon rubber having an opening 9 through which the pointed portion 3 projects. The jacket 7 is provided all around with substantially flat edge 11 which is also made of silicon rubber. The jacket 7 and the edge 11 preferably form one integral unit. The edge 11 extends in a plane perpendicular to the direction in which the pointed portion 3 projects. The surface 13 of the edge 11, engaging the skin of the patient when the electrode is applied, is preferably roughened. Present between the jacket 7 and the pointed portion 3 is a space in which a piece of spongy material 15, for example, fabric is clamped to cover the pointed portion. This sponge can be saturated with a conductive liquid or a known electrode paste to ensure proper electrical contact with the skin.

On the rear of the electrode there is provided a collar 17. Present between this collar and the edge 11 is a circular groove 19. The electrode can be fitted on an elastic band 12 by pressing the collar 17 through an opening in the band, after which the edge of the opening engages in the groove 19. This is illustrated in FIG. 2 which shows the electrode in the operating condition. The band 21 is tensioned about a leg 23 of a patient (cross-sectional view), so that the electrode is pressed into the tissue. The edge 11 is then distorted, so that it contacts the skin. Via a plug 25 and a cable 27, the electrode is connected to a stimulation apparatus (not shown). Elsewhere on the leg a second electrode, having a large surface, can be fitted; this electrode serves to close the current circuit and does not provide stimulation itself.

What is claimed is:

1. A skin electrode comprising
   a jacket of flexible insulating material having a central portion and a peripherally extending flat edge portion about said central portion for non-slipping contact with skin;
   an electrically conductive core extending through the central portion of said jacket and held thereby, said core having at one end a generally conically shaped pointed portion, an apical portion thereof protruding out of the plane of said flat edge portion of said jacket and pointing perpendicularly away therefrom, said core having means for making electrical contact thereto at the other end thereof; and
   spongy absorbent material covering at least said apical portion of said core, said jacket having a tapered annular flange extending from said central portion and surrounding said conically shaped portion of said core to leave a space therebetween, the peripheral region of said spongy material being received and held in said space between the flange and the conically shaped portion of said core, said annular flange forming a hole through which said spongy material covering said apical portion protrudes for contact with skin.

2. A skin electrode as defined in claim 1 wherein the material of said jacket is silicon rubber.

3. A skin electrode as defined in claim 1 wherein the surface of said flat edge portion of said jacket on the side where said spongy material protrudes is rough for non-slipping contact with skin.

4. A skin electrode as defined in claim 1 and further comprising an elastic band means for pressing said jacket against the skin of a patient.

* * * * *